United States Patent
Sampath et al.

(10) Patent No.: US 11,413,282 B2
(45) Date of Patent: *Aug. 16, 2022

(54) COMBINATION THERAPY OF A TYPE II ANTI-CD20 ANTIBODY WITH A SELECTIVE BCL-2 INHIBITOR

(71) Applicants: GENENTECH, INC., South San Francisco, CA (US); HOFFMANN-LA ROCHE INC., Little Falls, NJ (US); ABBVIE INC., North Chicago, IL (US)

(72) Inventors: Deepak Sampath, South San Francisco, CA (US); Christian Klein, Iffeldorf (DE); Wayne John Fairbrother, South San Francisco, CA (US)

(73) Assignees: GENENTECH, INC., South San Francisco, CA (US); HOFFMANN-LA ROCHE INC., Little Falls, NJ (US); ABBVIE INC., North Chicago, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/365,595

(22) Filed: Nov. 30, 2016

(65) Prior Publication Data

US 2017/0281619 A1 Oct. 5, 2017

Related U.S. Application Data

(63) Continuation of application No. 14/020,761, filed on Sep. 6, 2013, now Pat. No. 9,539,251.

(60) Provisional application No. 61/698,379, filed on Sep. 7, 2012.

(51) Int. Cl.
*A61K 31/496* (2006.01)
*A61P 35/02* (2006.01)
*A61P 35/00* (2006.01)

(52) U.S. Cl.
CPC .................. *A61K 31/496* (2013.01)

(58) Field of Classification Search
CPC ... A61K 31/496; A61K 31/495; A61K 39/395
USPC ..................................... 424/133.1
See application file for complete search history.

(56) References Cited

U.S. PATENT DOCUMENTS

| 7,767,684 | B2 | 8/2010 | Bruncko et al. |
| 8,173,811 | B2 | 5/2012 | Bruncko et al. |
| 8,546,399 | B2 | 10/2013 | Bruncko et al. |
| 9,174,982 | B2 | 11/2015 | Bruncko et al. |
| 9,539,251 | B2 * | 1/2017 | Sampath ............ A61K 31/496 |
| 10,993,942 | B2 * | 5/2021 | Sampath ............ A61K 31/496 |
| 11,110,087 | B2 * | 9/2021 | Sampath ............ A61K 31/496 |
| 2005/0123546 | A1 | 6/2005 | Umana et al. |
| 2008/0076779 | A1 | 3/2008 | Elmore et al. |
| 2009/0098118 | A1 | 4/2009 | Friess et al. |
| 2010/0305122 | A1 | 12/2010 | Bruncko et al. |
| 2012/0028925 | A1 | 2/2012 | Tao et al. |
| 2012/0108590 | A1 | 5/2012 | Birtalan et al. |
| 2012/0129853 | A1 | 5/2012 | Elmore et al. |
| 2012/0157470 | A1 | 6/2012 | Catron et al. |
| 2012/0277210 | A1 | 11/2012 | Catron et al. |
| 2014/0113910 | A1 | 4/2014 | Bruncko et al. |
| 2014/0275540 | A1 | 9/2014 | Chan et al. |
| 2016/0347852 | A1 | 12/2016 | Klein et al. |
| 2022/0008413 | A1 | 1/2022 | Sampath et al. |

FOREIGN PATENT DOCUMENTS

| WO | 2005044859 A2 | 5/2005 |
| WO | 2010138588 A2 | 12/2010 |

OTHER PUBLICATIONS

Busken et al., Digestive Disease Week Abstracts and Itinerary Planner, 2003, abstract No. 850 (2003).
Czuczman et al., "The future of CD20 monoclonal antibody therapy in B-cell malignancies", Leukemia & Lymphoma, 51(6):983-994 (2010).
Davids et al., "Targeting the B-cell lymphoma/leukemia 2 family in cancer," J. Clin Oncol., 30(25):3127-3135 (2012).
Flynn et al., "Preliminary Results of a Phase 1b Study (GP28331) Combining GDC-0199 (ABT-199) and Obinutuzumab in Patients with Relapsed/Refractory or Previously Untreated Chronic Lymphocytic Leukemia," Blood, 124(21) (2014).
Herting et al., Blood, 116(abstract# 3915):1-2 (2010).
International Search Report for PCT Application No. PCT/US2013/058557 completed on Oct. 24, 2013 (4 pages).
Kaiser, "Cancer. First pass at cancer genome reveals complex landscape", Science, 313(5792):1370 (2006).
MacAuley et al., "American Association for Cancer Research (AACR), 103rd, Annual meeting Chicago, Illinois," (Mar. 31-Apr. 4, 2012), Drugs of the Future 2012 Prous Science ESP, 37:6:451-455 (2012).
Mossner et al., "Increasing the efficacy of CD20 antibody therapy through the engineering of a new type II anti-CD20 antibody with enhanced direct and immune effector cell-mediated B-cell cytotoxicity", Blood, 115(22):4393-4402 (2010).
Sampath et al., "Abstract A245: Combination of the glycoengineered Type II CD20 antibody obinutuzumab (GA101), and the novel Bcl-2 selective inhibitor, ABT-199 (GDC-0199), results in superior in vitro and in vivo anti-tumor activity in models of B-cell malianancies," Mol Cancer Ther, 12 (11 Suppl) (2013).
Sampath et al., "Combination of the glycoengineered Type II CD20 antibody obinutuzumab (GA101) and The novel Bcl-2 selective Inhibitor GDC-0199 Results in superior In Vitro and In Vivo Anti-tumor activity in models of B-Cell Malignancies," Blood, 122(21) (2013).

(Continued)

*Primary Examiner* — Yan Xiao
(74) *Attorney, Agent, or Firm* — Jones Day

(57) ABSTRACT

The present invention is directed to a combination therapy involving a type II anti-CD20 antibody and a selective BCL-2 inhibitor for the treatment of a patient suffering from cancer, particularly, a CD20-expressing cancer.

10 Claims, 5 Drawing Sheets

Specification includes a Sequence Listing.

(56) References Cited

OTHER PUBLICATIONS

Taber's Cyclopedic Medical Dictionary, F.A. Davis Company, Philadelphia, p. 274 (1985).
Davids et al., "Targeting the B-Cell Lymphoma/Leukemia 2 Family in Cancer", Journal of Clinical Oncology, Sep. 1, 2012, pp. 3127-3135, vol. 30, issue No. 25.
Bottcher et al., 2012, "Minimal residual disease quantification is an independent predictor of progression-free and overall survival in chronic lymphocytic leukemia: a multivariate analysis from the randomized GCLLSG CLL8 trial," J Clin Oncol., 30(9):980-988.
Hallek et al., 2008, "Guidelines for the diagnosis and treatment of chronic lymphocytic leukemia: a report from the International Workshop on Chronic Lymphocytic Leukemia updating the National Cancer Institute-Working Group 1996 guidelines," Blood, 111(12):5446-5456 and Errata, Blood, 2008, 112(13):5259.
Hallek et al., 2010, "Addition of rituximab to fludarabine and cyclophosphamide in patients with chronic lymphocytic leukaemia: a randomised, open-label, phase 3 trial," Lancet, 376(9747):1164-1174.
Howard et al., 2011, "The tumor lysis syndrome," N Engl J Med., 364(19):1844-1854.
Kaplan et al., 1958, "Nonparametric Estimation from Incomplete Observations," Journal of the American Statistical Association, 53(282):457-481.
Laprevotte et al., 2013, "Recombinant human IL-15 transpresentation by B leukemic cells from chronic lymphocytic leukemia induces autologous NK cell proliferation leading to improved anti-CD20 immunotherapy," J Immunol., 191(7):3634-3640 with supplemental data.
Rawstron et al., 2007, "International standardized approach for flow cytometric residual disease monitoring in chronic lymphocytic leukaemia," Leukemia, 21(5):956-964.
Souers et al., 2013, "ABT-199, a potent and selective BCL-2 inhibitor, achieves antitumor activity while sparing platelets," Nat Med., 19(2):202-208.
Aggarwal et al., 2009, "Models for Prevention and Treatment of Cancer: Problems vs Promises," Biochem Pharmacol., vol. 78, issue No. 9, pp. 1083-1094 (Author Manuscript version) (27 pages).
Davids et al., 2012, "The BCL-2-Specific BH3-Mimetic ABT-199 (GDC-0199) Is Active and Well-Tolerated in Patients with Relapsed Non-Hodgkin Lymphoma: Interim Results of a Phase I Study," Meeting Abstract, 54th ASH Annual Meeting, Nov. 16, 2012, Blood, 120(21):Abstract 304 (3 pages).
Davids et al., 2013, "ABT-199: Taking Dead Aim at BCL-2," Cancer Cell, vol. 23, pp. 139-141.
Elmore, 2012, "ABT-199: A Potent and Selective Bcl-2 Inhibitor," Presentation, Session "New Drugs on the Horizon 2," Apr. 1, 2012, American Association for Cancer Research (AACR) 103rd Annual Meeting (Chicago, IL) (35 pages).
obinutuzumab_GA101-MeSH-NCBI (Sep. 7, 2009).
Prescribing Information for Venclextatm (venetoclax) tablets, for oral use, Apr. 2016 (25 pages).
Prescribing Information for Venclextatm (venetoclax) tablets, for oral use, revised Jul. 2019 (49 pages).
Roberts et al., 2012, "Selective Inhibition of BCL-2 is Active Against Chronic Lymphocytic Leukemia (CLL): First Clinical Experience with the BH3-Mimetic ABT-199 (GDC-0199)," Presentation, Jun. 16, 2012, 17th Congress of the European Hematology Association (Amsterdam, The Netherlands) (30 pages).
Roberts et al., 2012, "Selective Inhibition of BCL-2 is Active Against Chronic Lymphocytic Leukemia (CLL): First Clinical Experience with the BH3-Mimetic ABT-199," Meeting Abstract, 17th Congress of the European Hematology Association, Jun. 2012, Haematologica, 97(sl):Abstract 0546 on pp. 219-220 (5 pages).
Seymour et al., 2012, "The BCL-2-Specific BH3-Mimetic ABT-199 (GDC-0199) Is Active and Well-Tolerated in Patients with Relapsed/Refractory Chronic Lymphocytic Leukemia: Interim Results of a Phase I First-in-Human Study," Meeting Abstract, 54th ASH Annual Meeting, Nov. 16, 2012, Blood, 120(21):Abstract 3923 (3 pages).
Troy, 2009, "The End of Medical Miracles?" The Wall Street Journal, updated Jun. 1, 2009, [retrieved on Jun. 12, 2016]. Retrieved from the Internet <URL: http://www.wsj.com/articles/SB124389153780873939> (9 pages).
U.S. Appl. No. 17/395,366, filed Aug. 5, 2021, Sampath et al.

* cited by examiner

FIG 1/5
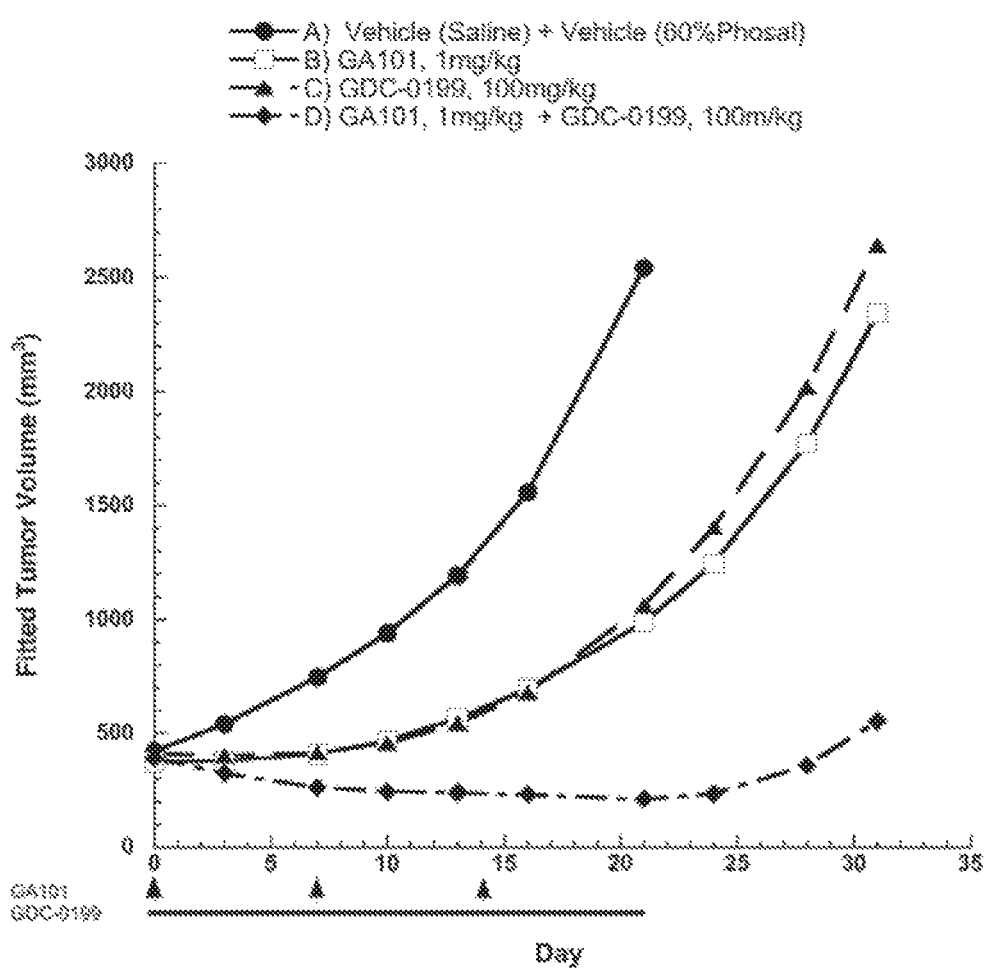

FIG 2/5
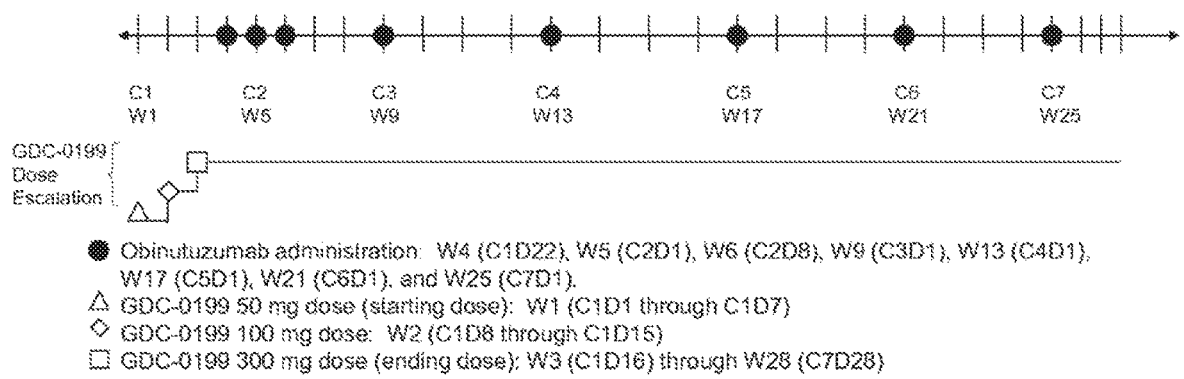
Schedule A Dosing Schema: GDC-0199 Step-Up Dosing for Three Weeks Before Starting Obinutuzumab
● Obinutuzumab administration: W4 (C1D22), W5 (C2D1), W6 (C2D8), W9 (C3D1), W13 (C4D1), W17 (C5D1), W21 (C6D1), and W25 (C7D1).
△ GDC-0199 50 mg dose (starting dose): W1 (C1D1 through C1D7)
◇ GDC-0199 100 mg dose: W2 (C1D8 through C1D15)
□ GDC-0199 300 mg dose (ending dose): W3 (C1D16) through W28 (C7D28)
C = cycle; D = day; W = week.

FIG 3/5

Schedule B Dosing Schema: Obinutuzumab Administered Before GDC-0199 Dose-Escalation

Cohort 1

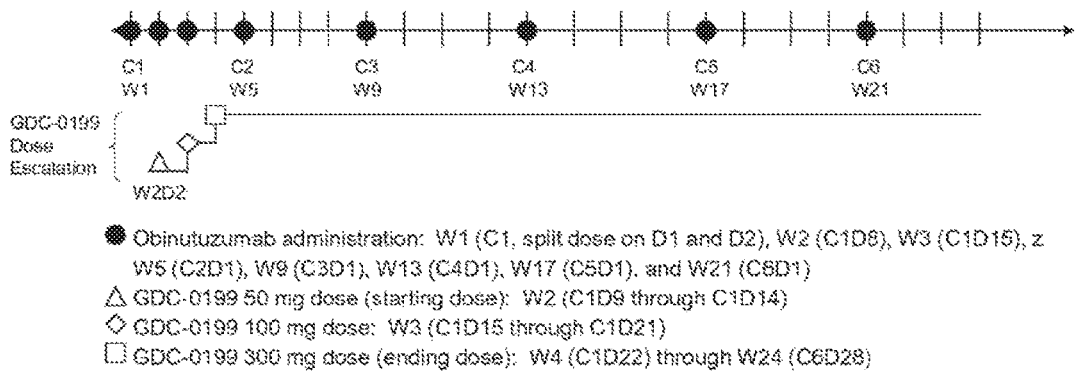

- Obinutuzumab administration: W1 (C1, split dose on D1 and D2), W2 (C1D8), W3 (C1D15), z W5 (C2D1), W9 (C3D1), W13 (C4D1), W17 (C5D1), and W21 (C6D1)
- △ GDC-0199 50 mg dose (starting dose): W2 (C1D9 through C1D14)
- ◇ GDC-0199 100 mg dose: W3 (C1D15 through C1D21)
- ☐ GDC-0199 300 mg dose (ending dose): W4 (C1D22) through W24 (C6D28)

Cohort 2

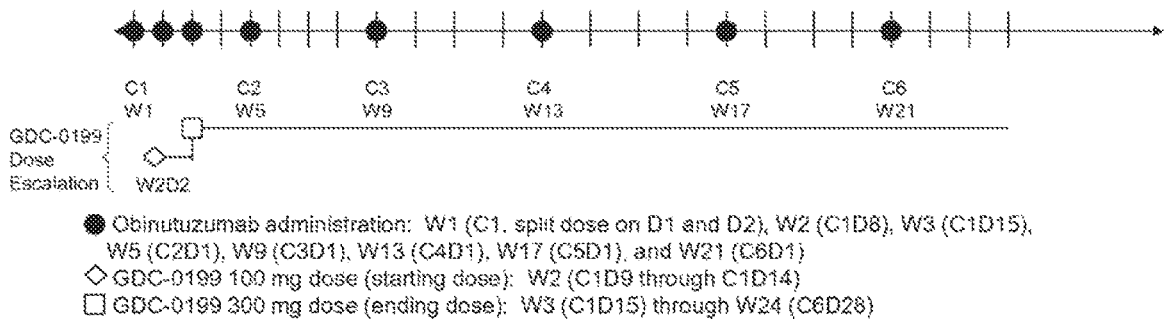

- Obinutuzumab administration: W1 (C1, split dose on D1 and D2), W2 (C1D8), W3 (C1D15), W5 (C2D1), W9 (C3D1), W13 (C4D1), W17 (C5D1), and W21 (C6D1)
- ◇ GDC-0199 100 mg dose (starting dose): W2 (C1D9 through C1D14)
- ☐ GDC-0199 300 mg dose (ending dose): W3 (C1D15) through W24 (C6D28)

Cohort 3

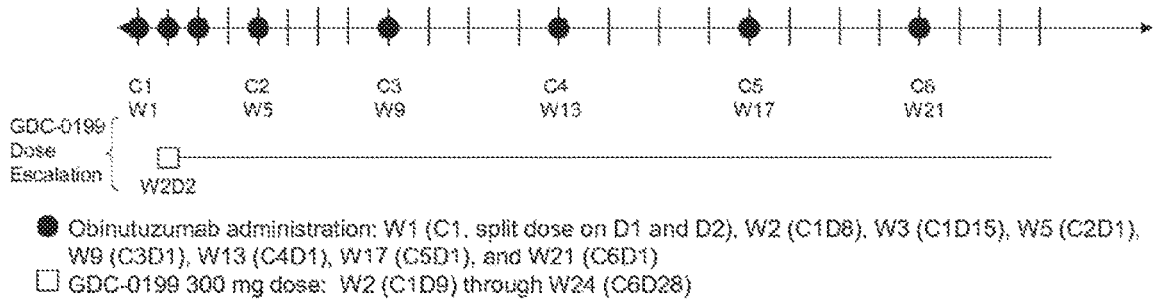

- Obinutuzumab administration: W1 (C1, split dose on D1 and D2), W2 (C1D8), W3 (C1D15), W5 (C2D1), W9 (C3D1), W13 (C4D1), W17 (C5D1), and W21 (C6D1)
- ☐ GDC-0199 300 mg dose: W2 (C1D9) through W24 (C6D28)

C = cycle; D = day; W = week.
Schedule B includes approximately three dosing cohorts to be enrolled sequentially.

FIG 4/5
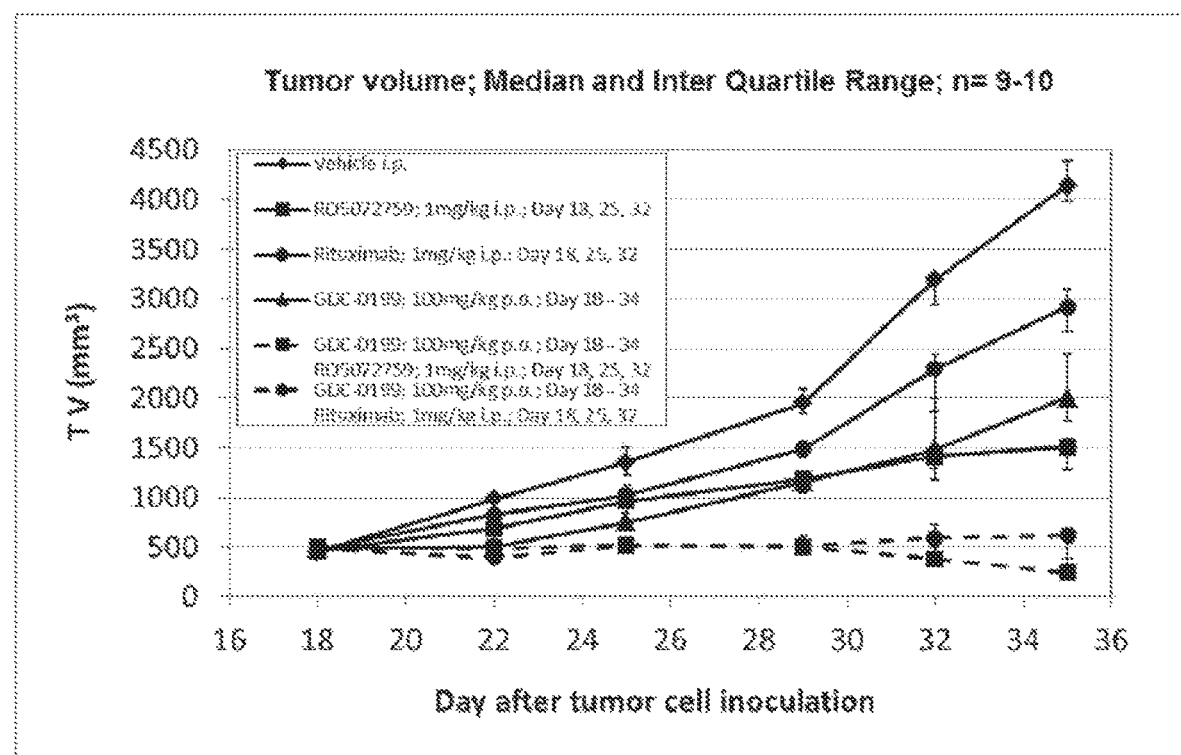

FIG 5/5
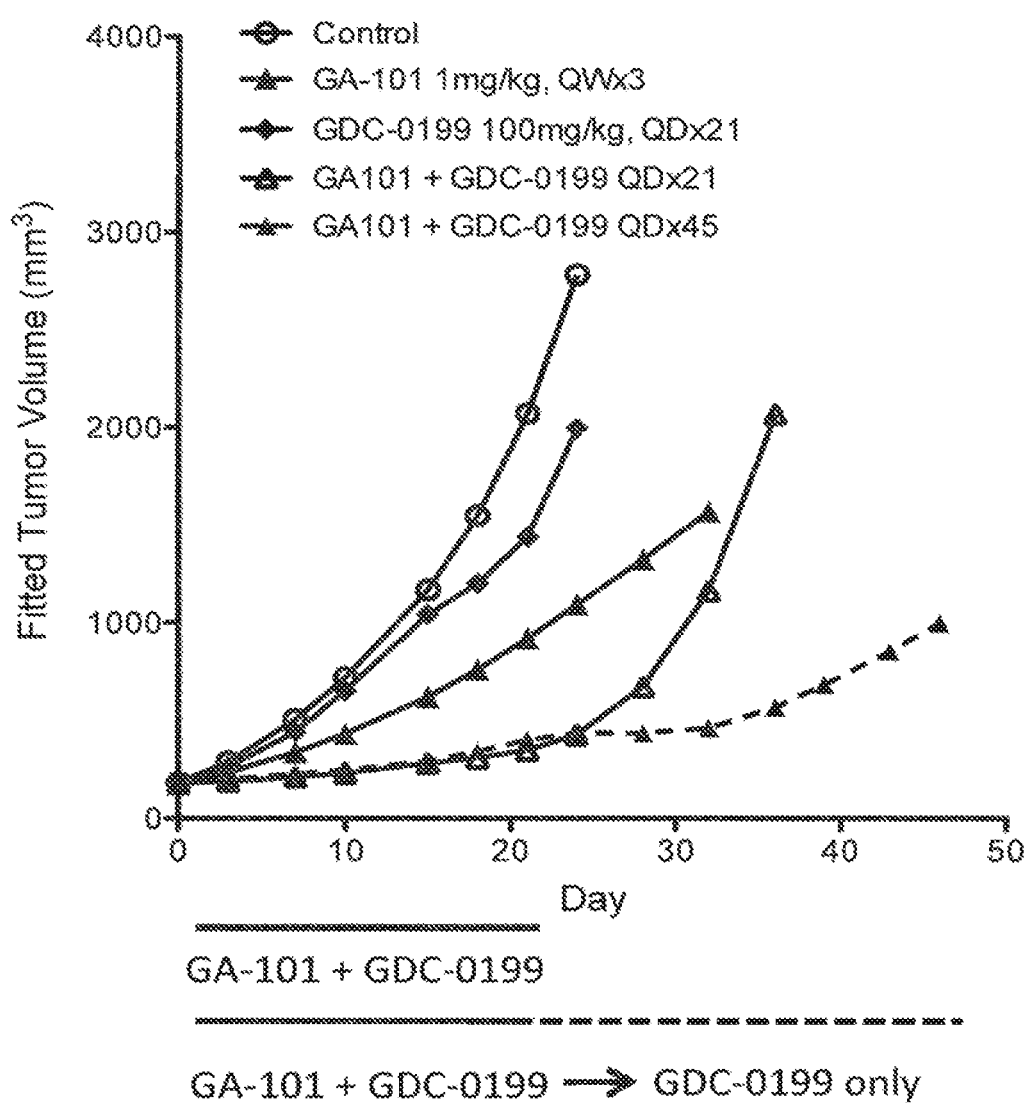

SEQUENCE LISTING

```
<160> NUMBER OF SEQ ID NOS: 10

<210> SEQ ID NO 1
<211> LENGTH: 6
<212> TYPE: PRT
<213> ORGANISM: Artificial
<220> FEATURE:
<223> OTHER INFORMATION: Sequence of HVR-H1 of GA101 Antibody

<400> SEQUENCE: 1

Gly Tyr Ala Phe Ser Tyr
1               5

<210> SEQ ID NO 2
<211> LENGTH: 8
<212> TYPE: PRT
```

```
<213> ORGANISM: Artificial
<220> FEATURE:
<223> OTHER INFORMATION: Sequence of HVR-H2 of GA101 Antibody

<400> SEQUENCE: 2

Phe Pro Gly Asp Gly Asp Thr Asp
1               5

<210> SEQ ID NO 3
<211> LENGTH: 10
<212> TYPE: PRT
<213> ORGANISM: Artificial
<220> FEATURE:
<223> OTHER INFORMATION: Sequence of HVR-H3 of GA101 Antibody

<400> SEQUENCE: 3

Asn Val Phe Asp Gly Tyr Trp Leu Val Tyr
1               5                   10

<210> SEQ ID NO 4
<211> LENGTH: 16
<212> TYPE: PRT
<213> ORGANISM: Artificial
<220> FEATURE:
<223> OTHER INFORMATION: Sequence of HVR-L1 of GA101 Antibody

<400> SEQUENCE: 4

Arg Ser Ser Lys Ser Leu Leu His Ser Asn Gly Ile Thr Tyr Leu Tyr
1               5                   10                  15

<210> SEQ ID NO 5
<211> LENGTH: 7
<212> TYPE: PRT
<213> ORGANISM: Artificial
<220> FEATURE:
<223> OTHER INFORMATION: Sequence of HVR-L2 of GA101 Antibody

<400> SEQUENCE: 5

Gln Met Ser Asn Leu Val Ser
1               5

<210> SEQ ID NO 6
<211> LENGTH: 9
<212> TYPE: PRT
<213> ORGANISM: Artificial
<220> FEATURE:
<223> OTHER INFORMATION: Sequence of HVR-L3 of GA101 Antibody

<400> SEQUENCE: 6

Ala Gln Asn Leu Glu Leu Pro Tyr Thr
1               5

<210> SEQ ID NO 7
<211> LENGTH: 119
<212> TYPE: PRT
<213> ORGANISM: Artificial
<220> FEATURE:
<223> OTHER INFORMATION: Sequence of VH of GA101 Antibody

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45
```

Gly Arg Ile Phe Pro Gly Asp Gly Asp Thr Asp Tyr Asn Gly Lys Phe
            50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
        115

<210> SEQ ID NO 8
<211> LENGTH: 115
<212> TYPE: PRT
<213> ORGANISM: Artificial
<220> FEATURE:
<223> OTHER INFORMATION: Sequence of VL of GA101 Antibody

<400> SEQUENCE: 8

Asp Ile Val Met Thr Gln Thr Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

Arg Thr Val
        115

<210> SEQ ID NO 9
<211> LENGTH: 448
<212> TYPE: PRT
<213> ORGANISM: Artificial
<220> FEATURE:
<223> OTHER INFORMATION: Sequence of Heavy Chain Full Sequence of GA101
      Antibody

<400> SEQUENCE: 9

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

```
Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 10
<211> LENGTH: 219
<212> TYPE: PRT
<213> ORGANISM: Artificial
<220> FEATURE:
<223> OTHER INFORMATION: Sequence of Light Chain Full Sequence of GA101
      Antibody

<400> SEQUENCE: 10

Asp Ile Val Met Thr Gln Thr Pro Leu Ser Leu Pro Val Thr Pro Gly
1               5                   10                  15
```

-continued

```
Glu Pro Ala Ser Ile Ser Cys Arg Ser Ser Lys Ser Leu Leu His Ser
            20                  25                  30
Asn Gly Ile Thr Tyr Leu Tyr Trp Tyr Leu Gln Lys Pro Gly Gln Ser
            35                  40                  45
Pro Gln Leu Leu Ile Tyr Gln Met Ser Asn Leu Val Ser Gly Val Pro
            50                  55                  60
Asp Arg Phe Ser Gly Ser Gly Ser Gly Thr Asp Phe Thr Leu Lys Ile
65                      70                  75                  80
Ser Arg Val Glu Ala Glu Asp Val Gly Val Tyr Tyr Cys Ala Gln Asn
                    85                  90                  95
Leu Glu Leu Pro Tyr Thr Phe Gly Gly Gly Thr Lys Val Glu Ile Lys
                100                 105                 110
Arg Thr Val Ala Ala Pro Ser Val Phe Ile Phe Pro Pro Ser Asp Glu
                115                 120                 125
Gln Leu Lys Ser Gly Thr Ala Ser Val Val Cys Leu Leu Asn Asn Phe
            130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                    165                 170                 175
Thr Tyr Ser Leu Ser Ser Thr Leu Thr Leu Ser Lys Ala Asp Tyr Glu
                180                 185                 190
Lys His Lys Val Tyr Ala Cys Glu Val Thr His Gln Gly Leu Ser Ser
                195                 200                 205
Pro Val Thr Lys Ser Phe Asn Arg Gly Glu Cys
210                 215
```

COMBINATION THERAPY OF A TYPE II ANTI-CD20 ANTIBODY WITH A SELECTIVE BCL-2 INHIBITOR

This application is a continuation of U.S. patent application Ser. No. 14/020,761, filed Sep. 6, 2013, which claims priority to U.S. Provisional No. 61/698,379, filed Sep. 7, 2012, the content of each of which is incorporated herein by reference in its entirety.

Incorporated herein by reference is the Sequence Listing being concurrently submitted via EFS-Web as an ASCII text file named "12655-135-999_SEQ LISTING", created Nov. 29, 2016, and being 9,829 bytes in size.

TECHNICAL FIELD

The present invention is directed to a combination therapy involving a type II anti-CD20 antibody and a selective Bcl-2 inhibitor for the treatment of a patient suffering from cancer, particularly a CD20-expressing cancer.

BACKGROUND

The CD20 molecule (also called human B-lymphocyte-restricted differentiation antigen or Bp35) is a hydrophobic transmembrane protein with a molecular weight of approximately 35 kD located on pre-B and mature B lymphocytes (Valentine, M. A., et al., J. Biol. Chem. 264 (19) (1989) 11282-11287; and Einfield, D. A., et al. EMBO J. 7(3) (1988) 711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson, K. C., et al., Blood 63(6) (1984) 1424-1433) but is not found on hematopoietic stem cells, pro-B cells, normal plasma cells, or other normal tissues (Tedder, T. F., et al., J, Immunol. 135(2) (1985) 973-979).

The 85 amino acid carboxyl-terminal region of the CD20 protein is located within the cytoplasm. The length of this region contrasts with that of other B cell-specific surface structures such as IgM, IgD, and IgG heavy chains or histocompatibility antigens class II a or β chains, which have relatively short intracytoplasmic regions of 3, 3, 28, 15, and 16 amino acids, respectively (Komaromy, M., et al., NAR II (1983) 6775-6785). Of the last 61 carboxyl-terminal amino acids, 21 are acidic residues, whereas only 2 are basic, indicating that this region has a strong net negative charge. The GenBank Accession No. is NP-690605. It is thought that CD20 might be involved in regulating an early step(s) in the activation and differentiation process of B cells (Tedder, T. F., et al., Eur. J. Immunol. 16 (1986) 881-887) and could function as a calcium ion channel (Tedder, T. F., et al., J. Cell. Biochem. 14D (1990) 195). There exist two different types of anti-CD20 antibodies which differ significantly in their mode of CD20 binding and biological activities (Cragg, M. S., et al., Blood 103 (2004) 2738-2743; and Cragg, M. S., et al., Blood 101 (2003) 1045-1052). Type I antibodies, as e.g. rituximab, are potent in complement mediated cytotoxicity, whereas type II antibodies, as e.g. Tositumomab (B1), 11B8, AT80 or humanized B-Ly1 antibodies, effectively initiate target cell death via caspase-independent apoptosis with concomitant phosphatidylserine exposure.

The shared common features of type I and type II anti-CD20 antibodies are summarized in Table 1 below.

TABLE 1

| Properties of type I and type II anti-CD20 antibodies | |
|---|---|
| type I anti-CD20 antibodies | type II anti-CD20 antibodies |
| type 1 CD20 epitope | type II CD20 epitope |
| Localize CD20 to lipid rafts | Do not localize CD20 to lipid rafts |
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |
| Apoptosis induction upon cross-linking | Strong cell death induction without cross-linking |

The Bcl-2 family of proteins regulates programmed cell death triggered by developmental cues and in response to multiple Stress signals (Cory. S., and Adams, J. M., Nature Reviews Cancer 2 (2002) 647-656; Adams, Genes und Development 17 (2003) 2481-2495; Danial, N. N., and Korsmeyer, S. J., Cell 116 (2004) 205-219). Whereas cell survival is promoted by Bcl-2 itself and several close relatives (Bcl-xL, Bcl-W, Mcl-1 and A1), which bear three or four conserved Bcl-2 homology (BH) regions, apoptosis is driven by two other sub-families. The initial signal for cell death is conveyed by the diverse group of BH3-only proteins, including Bad, Bid, Bim, Puma and Noxa, which have in common only the small BH3 interaction domain (Huang and Strasser, Cell 103 (2000) 839-842). However, Bax or Bak, multi-domain proteins containing BH1-BH3, are required for commitment to cell death (Cheng, W. X., et al., Genes and Development 15 148 (2001) 1-1486). When activated, they can permeabilize the outer membrane of mitochondria and release pro-apoptogenic factors (e.g. cytochrome C) needed to activate the caspases that dismantle the cell (Wang, K., Genes and Development 15 (2001) 2922-2933; (Adams, 2003 supra); Green, D. R., and Kroemer, G., Science 305 (2004) 626-629).

Interactions between members of these three factions of the Bcl-2 family dictate whether a cell lives or dies. When BH3-only proteins have been activated, for example, in response to DNA damage, they can bind via their BH3 domain to a groove on their pro-survival relatives (Sattler, et al., Science 275 (1997) 983-986). How the BH3-only and Bcl-2-like proteins control the activation of Bax and Bak, however, remains poorly understood (Adams, 2003 supra). Most attention has focused on Bax. This soluble monomeric protein (Hsu, Y. T., et al., Journal of Biological Chemistry 272 (1997) 13289-1 3834; Wolter, K. G., et al., Journal of Cell Biology 139 (1997) 1281-92) normally has its membrane targeting domain inserted into its groove, probably accounting for its cytosolic localization (Nechushtan, A., et al., EMBO Journal 18 (1999) 2330-2341; Suzuki, et al., Cell 103 (2000) 645-654; Schinzel, A., et al., J Cell Biol 164 (2004) 1021-1032). Several unrelated peptides/proteins have been proposed to modulate Bax activity, reviewed in Lucken-Ardjomande, S., and Martinou, J. C., J Cell Sci 118 (2005) 473-483, but their physiological relevance remains to be established. Alternatively, Bax may be activated via direct engagement by certain BH3-only proteins (Lucken-Ardjomande, S., and Martinou, J. C., 2005 supra), the best documented being a truncated form of Bid, tBid (Wei, M. C., et al., Genes and Development 14 (2000) 2060-2071; Kuwana, T., et al., Cell 111 (2002) 331-342; Roucou, X., et al., Biochemical Journal 368 (2002) 915-921; Cartron, P. F., et al., Mol Cell 16 (2004) 807-818). As discussed elsewhere (Adams 2003 supra), the oldest model, in which Bcl-2 directly engages Bax (Oltvai, Z. N., et al., Cell 74 (1993) 609-619), has become problematic because Bcl-2 is membrane bound while Bax is cytosolic, and their interaction seems highly dependent on the detergents used for cell lysis (Hsu, Y. T., and Youle, 1997 supra). Nevertheless, it is well established that the BH3 region of Bax can mediate association with Bcl-2 (Zha, H., and Reed, J., Journal of Biological Chemistry 272 (1997) 31482-88; Wang, K., et al., Molecular und Cellular Biology 18 (1998) 6083-6089) and that Bcl-2 prevents the oligomerization of Bax, even though no heterodimers can be detected (Mikhailov, V., et al., Journal of Biological Chemistry 276 (2001) 18361-18374). Thus, whether the pro-survival proteins restrain Bax activation directly or indirectly remains uncertain.

Although Bax and Bak seem in most circumstances to be functionally equivalent (Lindsten, T., et al., Molecular Cell 6 (2000) 1389-1399; Wei, M. C., et al., 2001 supra), substantial differences in their regulation would be expected from their distinct localization in healthy cells. Unlike Bax, which is largely cytosolic, Bak resides in complexes on the outer membrane of mitochondria and on the endoplasmic reticulum of healthy cells (Wei, M. C., et al., 2000 supra; Zong, W. X., et al., Journal of Cell Biology 162 (2003) 59-69). Nevertheless, on receipt of cytotoxic signals, both Bax and Bak change conformation, and Bax translocates to the organellar membranes, where both Bax and Bak then form homo-oligomers that can associate, leading to membrane permeabilization (Hsu, Y. T., et al., PNAS 94 (1997) 3668-3672; Wolter, K. G., et al., 1997 supra; Antonsson, B., et al., Journal of Biological Chemistry 276 (2001) 11615-11623; Nechushtan, A., et al., Journal of Cell Biology 153 (2001) 1265-1276; Wei, M. C., et al., 2001 supra; Mikhailov, V., et al., Journal of Biological Chemistry 278 (2003) 5367-5376).

There exist various Bcl-2 inhibitors, which all have the same property of inhibiting prosurvival members of the Bcl-2 family of proteins and are therefore promising candidates for the treatment of cancer. Such Bcl-2 inhibitors are e.g. Oblimersen, SPC-2996, RTA-402, Gossypol, AT-101, Obatoclax mesylate, A-371191, A-385358, A-438744, ABT-737, ABT-263, AT-101, BL-11, BL-193, GX-15-003, 2-Methoxyantimycin $A_3$, HA-14-1, KF-67544, Purpurogallin, TP-TW-37, YC-137 and Z-24, and are described e.g. in Zhai, D., et al., Cell Death and Differentiation 13 (2006) 1419-1421.

Smith, M. R., et al, Molecular Cancer Therapeutics 3(12) (2004) 1693-1699 and Ramanarayanan, J. et al., British Journal of Haematology 127(5) (2004) 519-530, refer to a combination of a type I anti-CD20 antibody (rituximab) with antisense Bcl-2 oligonucleotides (Oblimersen).

SUMMARY OF THE INVENTION

Provided herein are methods for the treatment of a patient suffering from cancer, comprising co-administering, to a patient in need of such treatment, a type II anti-CD20 antibody and a selective Bcl-2 inhibitor. The co-administration may be simultaneous or sequential in either order.

An example of the type II anti-CD20 antibody for use in the present invention is a GA101 antibody.

In an embodiment, the type II anti-CD20 antibody has increased antibody dependent cellular cytotoxicity (ADCC).

In an embodiment, at least 40% of the oligosaccharides of the Fc region of said type II anti-CD20 antibody are non-fucosylated.

In an embodiment, the selective Bcl-2 inhibitor is GDC-0199 (also known as ABT-199), or a pharmaceutically acceptable salt thereof.

In an embodiment, the cancer is a non-solid tumor.

In certain embodiments, methods are provided for the treatment of a cancer in a human in need thereof comprising administering to said human a GA101 antibody and/or GDC-0199 in multiple dosing cycles. In an embodiment, each dosing cycle of the multiple dosing cycle is for at least 1 week. In an embodiment, each dosing cycle of the multiple dosing cycle is for at 2, for at least 3, for at least 4, for at least 5, or for at least 6 weeks.

In an embodiment wherein the GA101 antibody and GDC-0199 are administered to the human in multiple dosing cycles, GA101 antibody can, for example, be administered once per dosing cycle for one or more dosing cycles of the multiple dosing cycles. The amount of GA101 administered per dose can, for example, be between about 300 mg to about 3000 mg, or between about 500 mg to about 3000 mg, or about 500 mg to about 1200 mg.

In an embodiment wherein the GA101 antibody and GDC-0199 are administered to the human in multiple dosing cycles, GDC-0199 can, for example, be administered each day in a dosing cycle for one or more dosing cycles of the multiple dosing cycles. In an embodiment, GDC-0199 is administered in fewer than all of the days of the initial dosing cycle, and is administered each day of the dosing cycles of the multiple dosing cycles that follow the initial dosing cycle. The amount of GDC-0199 administered per day can be between about 10 mg to about 1,000 mg, about 20 mg to about 800 mg, about 20 mg to about 500 mg, or between about 50 mg to about 300 mg.

In an embodiment, both the GA101 antibody and GDC-0199 are administered to the patient in at least 2, 3, 4, 5, 6, 7, 8, or more than 8, dosing cycles of the multiple dosing cycles.

In certain embodiments of the methods provided for the treatment of a cancer in a human in need thereof comprising administering to said human both a GA101 antibody and GDC-0199 in multiple dosing cycles, following the last dosing cycle of multiple dosing cycles, GDC-0199 alone can be administered to the human in the absence of the GA101 antibody, or the GA101 antibody alone can be administered to the patient in the absence of GDC-0199. For instance, when GDC-0199 is administered alone to the human (e.g., following the last cycle of multiple dosing cycles wherein both GDC-0199 and the GA101 antibody are administered to the human), GDC-0199 can be administered to the human for at least 3, 4, 5, 6, 7, 8 or 9 days, or for 10 or more days, for 20 or more days, or for 30 or more days.

In yet another embodiment of the methods provided wherein a GA101 antibody and GDC-0199 are administered to the patient in multiple dosing cycles, the multiple dosing cycles comprise an escalating dosing cycle in which GDC-0199 is administered to the patient in escalating daily dose amounts during the escalating dosing cycle.

DESCRIPTION OF THE FIGURES

FIG. 1. Antitumor activity of combined treatment of a type II anti-CD20 antibody (GA101 antibody, in this case, obinutuzumab) with a Bcl-2 inhibitor (ABT-199, a.k.a. GDC-0199). Arrows and line under the x-axis indicates the days of dosing of GA101 and GDC-0199, respectively.

FIG. 2. Exemplary dosing schedule for administering GDC-199 with obinutuzumab.

FIG. 3. Exemplary dosing schedule for administering GDC-199 with obinutuzumab.

FIG. 4. Antitumor activities of a type II anti-CD20 antibody (obinutuzumab, a.k.a. RO5072759) used alone or in combination with GDC-0199, and of a type I anti-CD20 antibody (rituximab) used alone or in combination with GDC-0199 on human Z138 mantle cell lymphoma cells.

FIG. 5. Results from xenograft model of aggressive lymphoma demonstrating that single agent treatment with GDC-0199 following combination of GDC-0199 with type II anti-CD20 antibody (GA101 antibody, in this case, obinutuzumab) delays tumor regrowth.

DETAILED DESCRIPTION OF THE INVENTION

The present invention relates to the method described above.

The present invention also relates to a method for the treatment of a human in need thereof comprising administering to said human an effective amount of a GA101 antibody or 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof for one or more dosing periods, followed by co-administering an effective amount of said GA101 antibody and 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof for one or more dosing periods.

The present invention also relates to a method for the treatment of a human in need thereof comprising administering to said human an effective amount of a GA101 antibody or 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide for 0, 1, 2, 3, 4, 5, 6, 7, 8, 9, 10, 11, 12, 13, or 14 days, followed by co-administering an effective amount of said GA101 antibody and 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof for one or more dosing periods.

The present invention also relates to a method for the treatment of a human in need thereof comprising administering an effective amount of said GA101 antibody for 1, 2, 3, 4, 5, 6, or 7 days, followed by co-administering an effective amount of said GA101 antibody antibody and 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof for one or more dosing periods.

The present invention also relates to a method for the treatment of a human in need thereof comprising administering an effective amount of 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof for 1, 2, 3, 4, 5, 6, or 7 days, followed by co-administering an effective amount of said GA101 antibody antibody and 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof for one or more dosing periods.

The present invention also relates to a method for the treatment of a human in need thereof comprising administering an effective amount of said GA101 antibody once every dosing period for 1, 2, 3, 4, 5 or 6 cycles, followed by co-administering an effective amount of said GA101 antibody antibody once every dosing period and 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino) phen or a pharmaceutically acceptable salt thereof one, two or three times a day for one or more dosing periods.

The present invention also relates to a method for the treatment of a human in need thereof comprising administering an effective amount of 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof one, two or three times a day for 1, 2, 3, 4, 5 or 6 dosing periods, followed by co-administering an effective amount of said GA101 antibody once every dosing period and 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof one, two or three times a day for one or more dosing periods.

The present invention also relates to any one of the above methods, wherein the effective amount of said GA101 antibody is 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 mg and the effective amount of 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof is 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 mg.

The present invention also relates to any one of the above methods, wherein the effective amount of said GA101 antibody is 800, 900, 1000, 1100, 1200, 1300, 1400 or 1500 mg, and the effective amount of 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof is 50, 60, 70, 80, 90, 100, 110, 120, 130, 140, 150, 160, 170, 180, 190, 200, 210, 220, 230, 240, 250, 260, 270, 280, 290 or 300 mg.

The present invention also relates to any one of the above methods, wherein when said cancer is NHL, the effective amount of said GA101 antibody is 800, 900, 1000, 1100, 1200, 1300, 1400 or 1500 mg, and the effective amount of 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof is 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530 540, 550, 560, 570, 580, 590, 600, 610, 620, 630, 640, 650, 660, 670, 680, 690, 700, 710, 720, 730, 740, 750, 760, 770, 780, 790, and 800 mg.

The present invention also relates to any one of the above methods, wherein when said cancer is AML, the effective amount of said GA101 antibody is 800, 900, 1000, 1100, 1200, 1300, 1400 or 1500 mg, and the effective amount of 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide or a pharmaceutically acceptable salt thereof is 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530 540, 550, 560, 570, 580, 590, 600, 610, 620, 630, 640, 650, 660, 670, 680, 690, 700, 710, 720, 730, 740, 750, 760, 770, 780, 790, and 800 mg.

The present invention also relates to any one of the above methods, wherein said GA10antibody and 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl) benzamide or a pharmaceutically acceptable salt thereof were co-administered sequentially during each dosing period, and each dosing period is 5, 6, 7, 8, 9, 10, 11, 12, 13, or 14 days.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

In one embodiment, said type II anti-CD20 antibody is a monoclonal antibody.

The term "chimeric antibody" refers to a monoclonal antibody comprising a variable region, i.e., binding region, from one source or species and at least a portion of a constant region derived from a different source or species, usually prepared by recombinant DNA techniques. Chimeric antibodies comprising a murine variable region and a human constant region are especially preferred. Such murine/human chimeric antibodies are the product of expressed immunoglobulin genes comprising DNA segments encoding murine immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric and bifunctional antibodies.

The term "human antibody", as used herein, is intended to include antibodies having variable and constant regions derived from human germline immunoglobulin sequences. Human antibodies are well-known in the state of the art (van Dijk, M. A., and van de Winkel, J. G., Curr. Opin. Pharmacol. 5 (2001) 368-374). Based on such technology, human antibodies against a great variety of targets can be produced. Examples of human antibodies are for example described in Kellermann, S. A., et al., Curr Opin Biotechnol. 13 (2002) 593-597.

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form. The recombinant human antibodies according to the invention have been subjected to in vivo somatic hypermutation. Thus, the amino acid sequences of the VH and VL regions of the recombinant antibodies are sequences that, while derived from and related to human germline VH and VL sequences, may not naturally exist within the human antibody germline repertoire in vivo.

As used herein, "specifically binding" or "binds specifically to" refers a binding that is sufficiently selective to a target as to distinguish it from a binding tounwanted or nonspecific targets (e.g., an antibody that specifically binds to a human CD20). In one embodiment, a GA101 antibody of this invention has a binding affinity for human CD20 (Kd) of $\leq 1$ µM, $\leq 100$ nM, $\leq 10$ nM, $\leq 1$ nM, $\leq 0.1$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In yet another embodiment, the KD is $10^{-10}$ mol/l or lower (e.g. $10^{-12}$ mol/l). The binding affinity is determined with a standard binding assay, such as Scatchard plot analysis on CD20 expressing cells.

The term "nucleic acid molecule", as used herein, is intended to include DNA molecules and RNA molecules. A nucleic acid molecule may be single-stranded or double-stranded. In one embodiment, it is double-stranded DNA.

The "constant domains" are not involved directly in binding the antibody to an antigen but are involved in the effector functions (ADCC, complement binding, and CDC).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W. H. Freeman and Co., page 91 (2007).)

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b(H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Synonyms of CD20, as recognized in the art, include B-lymphocyte antigen CD20, B-lymphocyte surface antigen B1, Leu-16, Bp35, BM5, and LF5.

The term "anti-CD20 antibody" according to the invention is an antibody that binds specifically to CD20 antigen. Depending on binding properties and biological activities of anti-CD20 antibodies to the CD20 antigen, two types of anti-CD20 antibodies (type I and type II anti-CD20 antibodies) can be distinguished according to Cragg, M. S., et al., Blood 103 (2004) 2738-2743; and Cragg, M. S., et al., Blood 101 (2003) 1045-1052, see Table 2.

TABLE 2

Properties of type I and type II anti-CD20 antibodies

| type I anti-CD20 antibodies | type II anti-CD20 antibodies |
| --- | --- |
| type I CD20 epitope | type II CD20 epitope |
| Localize CD20 to lipid rafts | Do not localize CD20 to lipid rafts |
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |

TABLE 2-continued

Properties of type I and type II anti-CD20 antibodies

| type I anti-CD20 antibodies | type II anti-CD20 antibodies |
| --- | --- |
| Apoptosis induction upon cross-linking | Strong cell death induction without cross-linking |

One property of type I and type II anti-CD20 antibodies is their mode of binding. Type I and type II anti-CD20 antibodies can be classified by the ratio of the binding capacities to CD20 on Raji cells (ATCC-No. CCL-86) of said anti-CD20 antibody compared to rituximab.

The type II anti-CD20 antibodies have a ratio of the binding capacities to CD20 on Raji cells (ATCC-No. CCL-86) of said anti-CD20 antibody compared to rituximab of 0.3 to 0.6, and in one embodiment of 0.35 to 0.55, and in another embodiment, 0.4 to 0.5. Examples of such type II anti-CD20 antibodies include e.g. tositumomab (B1 IgG2a), GA101antibody IgG1 (a chimeric humanized IgG1 antibody as disclosed in WO 2005/044859), 11B8 IgG1 (as disclosed in WO 2004/035607), and AT80 IgG1. In one embodiment, said type II anti-CD20 antibody is a monoclonal antibody that binds to the same epitope as GA101antibody (as disclosed in WO 2005/044859).

The "ratio of the binding capacities to CD20 on Raja cells (ATCC-No. CCL-86) of an anti-CD20 antibodies compared to rituximab" is determined by direct immunofluorescence measurement (the mean fluorescence intensities (MFI) is measured) using said anti-CD20 antibody conjugated with Cy5 and rituximab conjugated with Cy5 in a FACSArray (Becton Dickinson) with Raji cells (ATCC-No. CCL-86), as described in Example No. 2, and calculated as follows:

Ratio of the binding capacities to $CD20$ on Raji cells $$(ATCC\text{-No. } CCL\text{-}86) = \frac{MFI(Cy5\text{-anti-}CD20 \text{ antibody})}{MFI(Cy5\text{-rituximab})} \times \frac{Cy5\text{-labeling ratio}(Cy5\text{-rituximab})}{Cy5\text{-labeling ratio}(Cy5\text{-anti-}CD20 \text{ antibody})}$$

MFI is the mean fluorescent intensity. The "Cy5-labeling ratio" as used herein means the number of Cy5-label molecules per molecule antibody.

Typically said type II anti-CD20 antibody has a ratio of the binding capacities to CD20 on Raji cells (ATCC-No. CCL-86) of said second anti-CD20 antibody compared to rituximab of 0.3 to 0.6, and in one embodiment, 0.35 to 0.55, and in yet another embodiment, 0.4 to 0.5.

In one embodiment said type II anti-CD20 antibody, e.g., a GA101 antibody, has increased antibody dependent cellular cytotoxicity (ADCC).

By "antibody having increased antibody dependent cellular cytotoxicity (ADCC)", it is meant an antibody, as that term is defined herein, having increased ADCC as determined by any suitable method known to those of ordinary skill in the art. One accepted in vitro ADCC assay is as follows:

1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;

3) the assay is carried out according to following protocol:
   i) the PBMCs are isolated using standard density centrifugation procedures and are suspended at $5 \times 10^6$ cells/ml in RPMI cell culture medium;
   ii) the target cells are grown by standard tissue culture methods, harvested from the exponential growth phase with a viability higher than 90%, washed in RPMI cell culture medium, labeled with 100 micro-Curies of $^{51}Cr$, washed twice with cell culture medium, and resuspended in cell culture medium at a density of $10^5$ cells/ml;
   iii) 100 microliters of the final target cell suspension above are transferred to each well of a 96-well microliter plate;
   iv) the antibody is serially-diluted from 4000 ng/ml to 0.04 ng/ml in cell culture medium and 50 microliters of the resulting antibody solutions are added to the target cells in the 96-well microliter plate, testing in triplicate various antibody concentrations covering the whole concentration range above;
   v) for the maximum release (MR) controls, 3 additional wells in the plate containing the labeled target cells, receive 50 microliters of a 2% (VN) aqueous solution of non-ionic detergent (Nonidet, Sigma, St. Louis), instead of the antibody solution (point iv above);
   vi) for the spontaneous release (SR) controls, 3 additional wells in the plate containing the labeled target cells, receive 50 microliters of RPMI cell culture medium instead of the antibody solution (point iv above);
   vii) the 96-well microliter plate is then centrifuged at $50 \times g$ for 1 minute and incubated for 1 hour at 4° C.;
   viii) 50 microliters of the PBMC suspension (point i above) are added to each well to yield an effector-target cell ratio of 25:1 and the plates are placed in an incubator under 5% CO2 atmosphere at 37° C. for 4 hours;
   ix) the cell-free supernatant from each well is harvested and the experimentally released radioactivity (ER) is quantified using a gamma counter;
   x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point V above), and SR is the average radioactivity quantified (see point ix above) for the SR controls (see point vi above);
4) "increased ADCC" is defined as either an increase in the maximum percentage of specific lysis observed within the antibody concentration range tested above, and/or a reduction in the concentration of antibody required to achieve one half of the maximum percentage of specific lysis observed within the antibody concentration range tested above. In one embodiment, the increase in ADCC is relative to the ADCC, measured with the above assay, mediated by the same antibody, produced by the same type of host cells, using the same standard production, purification, formulation and storage methods, which are known to those skilled in the art, except that the comparator antibody (lacking increased ADCC) has not been produced by host cells engineered to overexpress GnTIII and/or engineered to have reduced expression from the fucosyltransferase 8 (FUT8) gene (e.g., including, engineered for FUT8 knock out).

Said "increased ADCC" can be obtained by, for example, mutating and/or glycoengineering of said antibodies. In one embodiment, the antibody is glycoengineered to have a biantennary oligosaccharide attached to the Fc region of the antibody that is bisected by GlcNAc, e.g., in WO 2003/011878 (Jean-Mairet et al); U.S. Pat. No. 6,602,684 (Umana et al.); US 2005/0123546 (Umana et al), Umana, P., et al., Nature Biotechnol. 17 (1999) 176-180). In another embodiment, the antibody is glycoengineered to lack fucose on the carbohydrate attached to the Fc region by expressing the antibody in a host cell that is deficient in protein fucosylation (e.g., Lec13 CHO cells or cells having an alpha-1,6-fucosyltransferase gene (FUT8) deleted or the FUT gene expression knocked down (see, e.g., Yamane-Ohnuki et al. Biotech. Bioeng. 87:614 (2004); Kanda, Y. et al., Biotechnol. Bioeng., 94(4):680-688 (2006); and WO2003/085107). In yet another embodiment, the antibody sequence has been engineered in its Fc region to enhance ADCC (e.g., in one embodiment, such engineered antibody variant comprises an Fc region with one or more amino acid substitutions at positions 298, 333, and/or 334 of the Fc region (EU numbering of residues)).

The term "complement-dependent cytotoxicity (CDC)" refers to lysis of human tumor target cells by the antibody according to the invention in the presence of complement. CDC can be measured by the treatment of a preparation of CD20 expressing cells with an anti-CD20 antibody according to the invention in the presence of complement. CDC is found if the antibody induces at a concentration of 100 nM the lysis (cell death) of 20% or more of the tumor cells after 4 hours. In one embodiment, the assay is performed with $^{51}Cr$ or Eu labeled tumor cells and measurement of released $^{51}Cr$ or Eu. Controls include the incubation of the tumor target cells with complement but without the antibody.

The term "GA101 antibody" as used herein refers to any one of the following antibodies that bind human CD20: (1) an antibody comprising an HVR-H1 comprising the amino acid sequence of SEQ ID NO: 1, an HVR-H2 comprising the amino acid sequence of SEQ ID NO:2, an HVR-H3 comprising the amino acid sequence of SEQ ID NO:3, an HVR-L1 comprising the amino acid sequence of SEQ ID NO:4, an HVR-L2 comprising the amino acid sequence of SEQ ID NO:5, and an HVR-L3 comprising the amino acid sequence of SEQ ID NO:6; (2) an antibody comprising a VH domain comprising the amino acid sequence of SEQ ID NO:7 and a VL domain comprising the amino acid sequence of SEQ ID NO:8, (3) an antibody comprising an amino acid sequence of SEQ ID NO: 9 and an amino acid sequence of SEQ ID NO: 10; (4) an antibody known as obinutuzumab, or (5) an antibody that comprises an amino acid sequence that has at least 95%, 96%, 97%, 98% or 99% sequence identity with amino acid sequence of SEQ ID NO:9 and that comprises an amino acid sequence that has at least 95%, 96%), 97%), 98%) or 99% sequence identity with an amino acid sequence of SEQ ID NO: 10. In one embodiment, the GA101 antibody is an IgG1 isotype antibody The oligosaccharide component can significantly affect properties relevant to the efficacy of a therapeutic glycoprotein, including physical stability, resistance to protease attack, interactions with the immune system, pharmacokinetics, and specific biological activity. Such properties may depend not only on the presence or absence, but also on the specific structures, of oligosaccharides. Some generalizations between oligosaccharide structure and glycoprotein function can be made. For example, certain oligosaccharide structures mediate rapid clearance of the glycoprotein from the bloodstream through interactions with specific carbohydrate binding proteins, while others can be bound by antibodies and trigger undesired immune reactions. (Jenkins, N., et al., Nature Biotechnol. 14 (1996) 975-981).

Mammalian cells are the preferred hosts for production of therapeutic glycoproteins, due to their capability to glycosylate proteins in the most compatible form for human application. (Cumming, D. A., et al., Glycobiology 1 (1991) 115-130; Jenkins, N., et al., Nature Biotechnol. 14 (1996) 975-981). Bacteria very rarely glycosylate proteins, and like other types of common hosts, such as yeasts, filamentous fungi, insect and plant cells, yield glycosylation patterns associated with rapid clearance from the blood stream, undesirable immune interactions, and in some specific cases, reduced biological activity. Among mammalian cells, Chinese hamster ovary (CHO) cells have been most commonly used during the last two decades. In addition to giving suitable glycosylation patterns, these cells allow consistent generation of genetically stable, highly productive clonal cell lines. They can be cultured to high densities in simple bioreactors using serum free media, and permit the development of safe and reproducible bioprocesses. Other commonly used animal cells include baby hamster kidney (BHK) cells, NSO— and SP2/0-mouse myeloma cells. More recently, production from transgenic animals has also been tested. (Jenkins, N., et al., Nature Biotechnol. 14 (1996) 975-981).

All antibodies contain carbohydrate structures at conserved positions in the heavy chain constant regions, with each isotype possessing a distinct array of N-linked carbohydrate structures, which variably affect protein assembly, secretion or functional activity. (Wright, A., and Monison, S. L., Trends Biotech. 15 (1997) 26-32). The structure of the attached N-linked carbohydrate varies considerably, depending on the degree of processing, and can include high-mannose, multiply-branched as well as biantennary complex oligosaccharides. (Wright, A., and Morrison, S. L., Trends Biotech. 15 (1997) 26-32). Typically, there is heterogeneous processing of the core oligosaccharide structures attached at a particular glycosylation site such that even monoclonal antibodies exist as multiple glycoforms. Likewise, it has been shown that major differences in antibody glycosylation occur between cell lines, and even minor differences are seen for a given cell line grown under different culture conditions. (Lifely, M. R., et al., Glycobiology 5 (1995) 813-822).

One way to obtain large increases in potency, while maintaining a simple production process and potentially avoiding significant, undesirable side effects, is to enhance the natural, cell-mediated effector functions of monoclonal antibodies by engineering their oligosaccharide component as described in Umana, P., et al., Nature Biotechnol. 17 (1999) 176-180 and U.S. Pat. No. 6,602,684. IgG1 type antibodies, the most commonly used antibodies in cancer immunotherapy, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32).

It was previously shown that overexpression in Chinese hamster ovary (CHO) cells of β(1,4)-N-acetylglucosaminyltransferase III ("GnTIII), a glycosyltransferase catalyzing the formation of bisected oligosaccharides, significantly increases the in vitro ADCC activity of an antineuroblastoma chimeric monoclonal antibody (chCE7) produced by the engineered CHO cells. (See Umana, P., et al., Nature Biotechnol. 17 (1999) 176-180; and WO 99/154342, the entire contents of which are hereby incorporated by reference). The antibody chCE7 belongs to a large class of unconjugated monoclonal antibodies which have high tumor affinity and specificity, but have too little potency to be clinically useful when produced in standard industrial cell lines lacking the GnTIII enzyme (Umana, P., et al., Nature Biotechnol. 17 (1999) 176-180). That study was the first to show that large increases of ADCC activity could be obtained by engineering the antibody producing cells to express GnTIII, which also led to an increase in the proportion of constant region (Fc)-associated, bisected oligosaccharides, including bisected, non-fucosylated oligosaccharides, above the levels found in naturally-occurring antibodies.

In one embodiment, a composition comprising a GA101 antibody of this invention comprises GA101 antibodies engineered to have increased ADCC activity.

The term "Bcl-2" as used herein refers to the Bcl-2 protein (Swiss Prot ID No. P10415), a member of the Bcl-2 family of proteins (Cory, S., and Adams, J. M., Nature Reviews Cancer 2 (2002) 647-656; Adams, Genes und Development 17 (2003) 2481-2495; Danial, N. N., and Korsmeyer, S. J., Cell 116 (2004) 205-219; Petros, A. M., Biochim Biophys Acta 1644 (2004) 83-94).

The term "selective Bcl-2 inhibitors" as used herein refers to 2-(2H-pyrrolo[2,3-b]pyridin-4-yloxy)-4-((2-(4-chlorophenyl)-4,4-dimethyleyclohex-1-enyl)methyl)piperazin-1-yl)-N-(3-nitro-4-((tetrahydro-2H-pyran-4-yl)methylamino)phenylsulfonyl)benzamide (a.k.a. ABT-199 or GDC-0199), a Bcl-2 inhibitor of formula I, which is described in International Publication No. WO2010/138588 and in US publication NO. US2010/0305122, which are incorporated by reference herein.

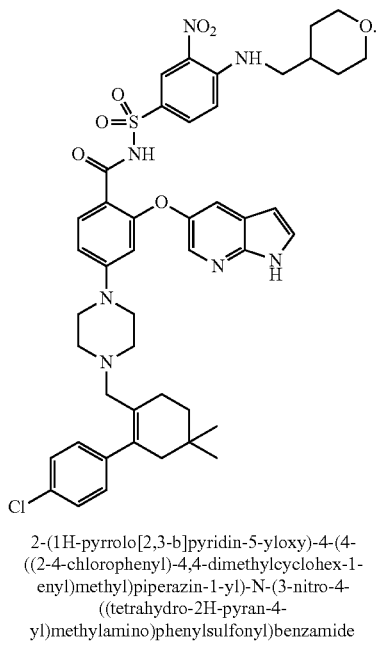

Formula I 2-(1H-pyrrolo[2,3-b]pyridin-5-yloxy)-4-(4-
((2-4-chlorophenyl)-4,4-dimethylcyclohex-1-
enyl)methyl)piperazin-1-yl)-N-(3-nitro-4-
((tetrahydro-2H-pyran-4-
yl)methylamino)phenylsulfonyl)benzamide The term "expression of the CD20" antigen is intended to indicate an significant level of expression of the CD20 antigen in a cell, e.g., a T- or B-Cell. In one embodiment, patients to be treated according to the methods of this invention express significant levels of CD20 on a B-cell tumor or cancer. Patients having a "CD20 expressing cancer" can be determined by standard assays known in the art. e.g. CD20 antigen expression is measured using immunohistochemical (IHC) detection, FACS or via PCR-based detection of the corresponding mRNA.

The term "CD20 expressing cancer" as used herein refers to all cancers in which the cancer cells show an expression of the CD20 antigen. Such CD20 expressing cancer may be, for example, lymphomas, lymphocytic leukemias, lung cancer, non small cell lung (NSCL) cancer, bronchioloaviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma, including refractory versions of any of the above cancers, or a combination of one or more of the above cancers.

In one embodiment, CD20 expressing cancer as used herein refers to lymphomas (e.g., B-Cell Non-Hodgkin's lymphomas (NHL)) and lymphocytic leukemias. Such lymphomas Lymphomas/ Burkitt's lymphoma (including endemic Burkitt's lymphoma, sporadic Burkitt's lymphoma and Non-Burkitt's lymphoma) c) marginal zone lymphomas (including extranodal marginal zone B cell lymphoma (Mucosa-associated lymphatic tissue lymphomas, MALT), nodal marginal zone B cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma) f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B-cell prolymphocytic leukemia, i) plasma cell neoplasms, plasma cell myeloma, multiple myeloma, plasmacytoma, j) Hodgkin's disease, k) acute myeloid leukemia (AML); among other types of lymphomas and lymphocyctic luekemias.

In one embodiment, the CD20 expressing cancer is a B-Cell Non-Hodgkin's lymphomas (NHL). In another embodiment, the CD20 expressing cancer is a Mantle cell lymphoma (MCL), acute lymphocytic leukemia (ALL), chronic lymphocytic leukemia (CLL), B-cell diffuse large cell lymphoma (DLCL), acute myeloid leukemia (AML), Burkitt's lymphoma, hairy cell leukemia, follicular lymphoma, multiple myeloma, marginal zone lymphoma, post transplant lymphoproliferative disorder (PTLD), HIV associated lymphoma, Waldenstrom's macroglobulinemia, or primary CNS lymphoma.

"Relapsed or Refractory" CLL as used herein includes CLL patients who have received at least 1 prior chemotherapy containing treatment regimen. Relapsed patients generally have developed progressive disease following a response to the prior chemotherapy-containing treatment regimen. Refractory patients have generally failed to respond or relapsed within 6 months to the last prior chemotherapy-containing regimen.

"Previously untreated" CLL as used herein includes patients diagnosed with CLL, but who have, in general, received no prior chemotherapy or immunotherapy. Patients with a history of emergency, loco-regional radiotherapy (e.g., for relief of compressive signs or symptoms) or corticosteroids can still be considered previously untreated.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The term "a method of treating" or its equivalent, when applied to, for example, cancer refers to a procedure or course of action that is designed to reduce or eliminate the number of cancer cells in a patient, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of a patient, is nevertheless deemed to induce an overall beneficial course of action. The terms "co-administration" or "co-administering" refer to the administration of said type II anti-CD20 antibody and said selective Bcl-2 inhibitor as two separate formulations. The co-administration can be simultaneous or sequential in either order. In one further embodiment, there is a time period while both (or all) active agents simultaneously exert their biological activities. Said type II anti-CD20 antibody and said selective Bcl-2 inhibitor are co-administered either simultaneously or sequentially (e.g. via an intravenous (i.v.) through a continuous infusion (one for the antibody and eventually one for the Bcl-2 inhibitor; or the Bcl-2 inhibitor is administered orally). When both therapeutic agents are co-administered sequentially the agents are administered in two separate administrations that are separated by a "specific period of time". The term specific period of time is meant any where from 1 hour to 15 days. For example, one of the agents can be administered within about 15, 14, 13, 12, 11, 10, 9, 8, 7, 6, 5, 4, 3, 2, or 1 day, or 24, 23, 22, 21, 20, 19, 18, 17, 16, 15, 14, 13, 12, 11, 10, 9, 8, 7, 6, 5, 4, 3, 2 or 1 hour from the administration of the other agent, and, in one embodiment, the specific period time is 10, 9, 8, 7, 6, 5, 4, 3, 2, or 1 day, or 24, 23, 22, 21, 20, 19, 18,17,16,15,14,13, 12, 11, 10, 9, 8, 7, 6, 5, 4, 3, 2 or 1 hour.

The term "simultaneously" means at the same time or within a short period of time, usually less than 1 hour.

A dosing period as used herein is meant a period of time, during which each therapeutic agent has been administered at least once. A dosing cycle is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, and, in one embodiment, 6, 7, 8, 9, 10, 11, 12, 13, or 14 days, for example, 7 or 14 days.

In certain embodiments, a dosing period is a dosing cycle.

It is self-evident that the antibodies are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician. The administration of an effective amount of a therapeutically agent can be a single administration or split dose administration, "split dose administration" is meant an effective amount is a split into multiple doses, preferably 2, and administered within 1 or 2 days. For example, if 100 mg of a selective BCL-2 inhibitor is deemed effective, it can be administered in one 100 mg administration or two 50 mg administrations. Split dose administration is sometimes desirable at the beginning of a dosing period to reduce side effects. When an effective amount is administered in split dosing, it is still considered one administration of an effective amount. For example, when 100 mg is the effective amount of a selective Bcl-2 inhibitor and that amount is administered in two 50 mg doses over a period of time, e.g. 2 days, only one effective amount is administered during that period of time.

The amount of co-administration of said type II anti-CD20 antibody and said Bcl-2 inhibitor and the timing of co-administration will depend on the type (species, gender, age, weight, etc.) and condition of the patient being treated and the severity of the disease or condition being treated. Said type II anti-CD20 antibody and said Bcl-2 inhibitor are suitably co-administered to the patient at one time or over a series of treatments. Depending on the type and severity of the disease, about 1 μg/kg to 50 mg/kg (e.g. 0.1-20 mg/kg) of said type II anti-CD20 antibody, and 0.1 mg/kg to 200 mg/kg (e.g. 10-150 mg/kg) of said selective Bcl-2 inhibitor is an initial candidate dosage for co-administration of both drugs to the patient. If the administration is intravenous the initial infusion time for said type II anti-CD20 antibody or said Bcl-2 inhibitor may be longer than subsequent infusion times, for instance approximately 90 minutes for the initial infusion, and approximately 30 minutes for subsequent infusions (if the initial infusion is well tolerated).

In one embodiment, the preferred dosage of said type II anti-CD20 antibody will be in the range from about 0.05 mg/kg to about 30 mg/kg, preferably 1 mg/kg to 30 mg/kg; or 500 mg-3000 mg flat dose. Thus, one or more doses of about 0.5 mg/kg, 2.0 mg/kg, 4.0 mg/kg, 10 mg/kg or 30 mg/kg or 500 mg-3000 mg flat dose (or any combination thereof) may be co-administered to the patient. The preferred dosage of said Bcl-2 inhibitor will be in the range from 20 mg/kg to about 150 mg/kg, preferably 1 mg/kg to 10 mg/kg. Depending on the on the type (species, gender, age, weight, etc.) and condition of the patient and on the type of anti-CD20 antibody and Bcl-2 inhibitor, the dosage and the administration schedule of said anti-CD20 antibody can differ from the dosage of Bcl-2 inhibitor. E.g. the said anti-CD20 antibody may be administered e.g. every one to three weeks and said Bcl-2 inhibitor may be administered daily or every 2 to 7 days. An initial higher loading dose, followed by one or more lower doses may also be administered.

The present invention relates in part to a composition comprising a type II anti-CD20 antibody and a selective Bcl-2 inhibitora selective Bcl-2 inhibitor.

In a preferred embodiment, the composition of the present invention is useful for preventing or reducing metastasis or further dissemination in such a patient suffering from CD20 expressing cancer. The composition is useful for increasing the duration of survival of such a patient, increasing the progression free survival of such a patient, increasing the duration of response, resulting in a statistically significant and clinically meaningful improvement of the treated patient as measured by the duration of survival, progression free survival, response rate or duration of response. In a preferred embodiment, the composition is useful for increasing the response rate in a group of patients.

In the context of this invention, additional other cytotoxic, chemotherapeutic or anti-cancer agents, or compounds that enhance the effects of such agents (e.g. cytokines) may be used in the type II anti-CD20 antibody and Bcl-2 inhibitor combination treatment of CD20 expressing cancer. Such molecules are suitably present in combination in amounts that are effective for the purpose intended. Preferably the type II anti-CD20 antibody and Bcl-2 inhibitor combination treatment is used without such additional cytotoxic, chemotherapeutic or anti-cancer agents, or compounds that enhance the effects of such agents.

Such agents include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP 16; e.g. VEPESID®), 6-mercaptopurine (6MP), 6-thioguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and paclitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil. Preferably the type II anti-CD20 antibody and Bcl-2 inhibitor combination treatment is used without such additional agents.

The use of the cytotoxic and anticancer agents described above as well as antiproliferative target-specific anticancer drugs like protein kinase inhibitors in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

In the context of this invention, an effective amount of ionizing radiation may be carried out and/or a radiopharmaceutical may be used in addition to the type II anti-CD20 antibody and Bcl-2 inhibitor combination treatment of CD20 expressing cancer. The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Is also possible to label the antibody with such radioactive isotopes. Preferably the type II anti-CD20 antibody and Bcl-2 inhibitor combination treatment is used without such ionizing radiation.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in WO 99/60023.

The type II anti-CD20 antibodies are administered to a patient according to known methods, by intravenous administration as a bolus or by continuous infusion over a period of time, by intramuscular, intraperitoneal, intracerobrospinal, subcutaneous, intra-articular, intrasynovial, or intrathecal routes. Intravenous or subcutaneous administration of the antibodies is preferred.

The Bcl-2 inhibitors are administered to a patient according to known methods, e.g. by intravenous administration as a bolus or by continuous infusion over a period of time, by intramuscular, intraperitoneal, intracerobrospinal, subcutaneous, intra-articular, intrasynovial, intrathecal, or peroral routes. Intravenous, subcutaneous or oral administration of the Bcl-2 inhibitors is preferred.

The invention also relates to a kit comprising a type II anti-CD20 antibody and a selective Bcl-2 inhibitor for the combination treatment of a patient suffering from a CD20 expressing cancer.

In an embodiment of the present invention, the kit further comprises a pharmaceutically acceptable carrier. The kit may further include a sterile diluent, which is preferably stored in a separate additional container. The kit may further include a package insert comprising printed instructions directing the use of the combined treatment as a method for a CD20 expressing cancer disease, preferably a B-Cell Non-Hodgkin's lymphoma (NHL).

The term "package insert" refers to instructions customarily included in commercial packages of therapeutic products, which may include information about the indications, usage, dosage, administration, contraindications and/or warnings concerning the use of such therapeutic products.

In a preferred embodiment, the article of manufacture containers may further include a pharmaceutically acceptable carrier. The article of manufacture may further include a sterile diluent, which is preferably stored in a separate additional container.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Pharmaceutical Compositions and Methods

Pharmaceutical compositions can be obtained by processing the type II anti-CD20 antibody or the anti-Bcl-2 active agent according to this invention with pharmaceutically acceptable, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Said pharmaceutical composition may further comprise one or more pharmaceutically acceptable carriers.

The present invention further provides a pharmaceutical composition, in particular for use in cancer, comprising (i) an effective first amount of a type II anti-CD20 antibody, or (ii) an effective second amount of a selective Bcl-2 inhibitor. Such composition optionally comprises pharmaceutically acceptable carriers and/or excipients.

Pharmaceutical compositions of the type II anti-CD20 antibody alone used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Pharmaceutical compositions of the anti-Bcl-2 active agent alone, e.g. the Bcl-2 inhibitor, depend on their pharmaceutical properties; e.g. for small chemical compounds such as e.g. ABT-737, ABT-199 or ABT-263, one formulation could be e.g. the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellouse | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

In one further embodiment of the invention the pharmaceutical compositions according to the invention are two separate formulations for said type II anti-CD20 antibody and said Bcl-2 inhibitor.

The active ingredients may also be entrapped in microcapsules prepared, for example, by coacervation techniques or by interracial polymerization, for example, hydroxymethylcellulose or gelatin-microcapsules and poly- (methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-gly colic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

The invention relates in part to a method for the treatment of a patient suffering from cancer, particularly a CD20-expressing cancer, comprising co-administering, to a patient in need of such treatment, a type II anti-CD20 antibody and a selective Bcl-2 inhibitor. Said type II anti-CD20 antibody and anti-Bcl-2 active agent are administered in effective amounts.

In certain embodiments, a dosing cycle is for 28 days.

In certain embodiments of a method of treating cancer in a patient as provided herein, the method comprises administering the type II anti-CD20 antibody and the selective Bcl-2 for one or more dosing cycles to the patient. In one embodiment, the one or more dosing cycles each last for at least one week. In another embodiment, the one or more dosing cycles are each for at least two weeks, three weeks, four weeks, five weeks, six weeks, seven weeks, eight weeks, nine weeks, or for more than nine weeks. In one embodiment, each dosing cycle is four weeks.

In one embodiment, the therapeutic agents are administered to the patient for one dosing cycle.

In another embodiment, therapeutic agents are administered to the patient for more than one dosing cycle, for instance, for two, three, four, five, six, seven or more than seven dosing cycles. As an example, where a dosing cycle is four weeks, and the patient is administered with one or both therapeutic agents over six dosing cycles, the treatment regimen will be for 24 weeks, such as illustrated in the dosing schemes shown in FIG. 3. In certain embodiments, methods are provided for the treatment of a cancer in a patient in need thereof comprising administering to said human a GA101 antibody and/or GDC-0199 in multiple dosing cycles.

In certain embodiments, the GA101 antibody and GDC-0199 are both administered to the patient in one or more dosing cycles of the multiple dosing cycles, and one of the GA101 antibody and GDC-0199 are administered in one or more dosing cycles of the multiple dosing cycles.

In certain embodiments of the methods of treatment provided herein, the therapeutic agents are administered to the patent in a dosing scheme comprising two or three treatment phases, where each treatment phase comprises at least one dosing cycle that differs from the dosing cycle from other treatment phases. For example, in one embodiment where the dosing cycle comprises four weeks, the type II anti-CD20 antibody can be administered to the patient once a week for two or more weeks of the first dosing cycle (e.g., a first treatment phase), and administered once per dosing cycle in the dosing cycles that follow the first dosing cycle (e.g., a second treatment phase).

In certain embodiments of the methods of treatment provided herein, the type II anti-CD20 antibody is administered to the patient once a week for at least one week of a dosing cycle. In some embodiments, where the dosing cycle is for two or more weeks, the the type II anti-CD20 antibody is administered to the patient once per dosing cycle.

In certain embodiments of the methods of treatment provided herein, GDC-0199 is administered once per day of a dosing cycle.

Both GDC-0199 and the type II anti-CD20 antibody can, for example, be administer to the patient in a dosing cycle. In certain dosing cycles, one therapeutic agent alone is administered to the patient.

In certain embodiments of the methods provided wherein the therapeutic agents are administered to the patent in a dosing scheme comprising multiple dosing cycles, the multiple dosing cycles comprise a first treatment phase having dosing cycles wherein in each dosing cycle the type II anti-CD20 antibody is administered once per dosing cycle and GDC-0199 is administered each day of the dosing cycle. Such dosing cycles in the first treatment phase can, for example, each be for four weeks. In some embodiments, the multiple dosing cycles can further comprise a second treatment phase wherein the type II anti-CD20 antibody alone is administered to the patient or wherein GDC-0199 alone is administered to the patient (e.g., a maintenance phase).

In some embodiments of the methods provided herein wherein the type II anti-CD20 antibody and GDC-0199 are both administered to the patient for one or more dosing cycles (e.g., in a treatment phase), the patient can then be administered with GDC-0199 alone (e.g., in a maintenance phase).

In certain embodiments where GDC-0199 alone is administered to the patient following combination therapy, GDC-0199 can, for example, be administered once a day, once every other day, once every three days, four, five or six days, or once a week, to the patient.

In certain embodiments wherein the type II anti-CD20 antibody alone is administered to the patient following combination therapy, the type II anti-CD20 antibody can, for example, be administered once a week, once every two weeks or once per month, to the patient.

In certain embodiments of the methods of treatment provided herein, the amounts of GDC-0199 per dose administered to the patient are increased during a first dosing cycle. See, e.g., FIG. 2 for an exemplary dosing scheme where amounts of GDC-0199 administered to patients in the first dosing cycle escalate from 50 mg doses the first week, to 100 mg doses the second week, to 300 mg doses the third week).

In certain embodiments, escalating doses of GDC-0199 are administered to the patient prior to administration of the type II anti-CD20 antibody. In other embodiments, escalating doses of GDC-0199 are administered to the patient after the type II anti-CD20 antibody has been administered to the patient.

In some embodiments of the method of treatment provided herein, the amount of GDC-0199 administered to the patient per dose is increased during the first dosing cycle from initial amounts of between 10 mg to 80 mg to final amounts of between 190 mg to 400 mg. In certain embodiments, the amount of GDC-0199 per dose administered to the patients begins with 50 mg or 100 mg, and is increased to 300 mg per dose. In some embodiments, the amount of GDC-0199 in the initial doses administered to the patient can, for example, be between 20 mg to 60 mg (e.g., 20 mg, 25 mg, 30 mg, 35 mg, 40 mg, 45 mg, 50 mg, 55 mg or 60 mg doses), followed by dose amounts of 100 mg, 200 mg, 300 mg or more of GDC-0199.

In certain embodiments of the methods provided herein, doses of GDC-0199 are administered to the patient in increasing amounts prior to the first administration of the type II anti-CD20 antibody. In some embodiments, doses of GDC-0199 are administered to the patient in increasing amounts after the first administration of the type II anti-CD20 antibody.

As used herein, the term "patient" typically refers to a human in need of treatment with type II anti-CD20 antibody (e.g. a patient suffering from CD20 expressing cancer) for any purpose, and, in one embodiment, a human in need of such a treatment to treat cancer, or a precancerous condition or lesion. However, the term "patient" can also refer to non-human animals, preferably mammals such as dogs, cats, horses, cows, pigs, sheep and non-human primates, among others.

The invention further comprises a type II anti-CD20 antibody for the treatment of CD20 expressing cancer in combination with a selective Bcl-2 inhibitor.

The invention further comprises a type II anti-CD20 antibody for the treatment of a patient suffering from a CD20 expressing cancer in combination a selective Bcl-2 inhibitor.

The invention further comprises a type II anti-CD20 antibody and a selective Bcl-2 inhibitor for use in the treatment of CD20 expressing cancer.

The invention further comprises a type II anti-CD20 antibody and a selective Bcl-2 inhibitor for use in the treatment of a patient suffering from a CD20 expressing cancer.

In one embodiment, said selective Bcl-2 inhibitor is ABT-199.

In one embodiment, said type II anti-CD20 antibody has a ratio of the binding capacities to CD20 on Raji cells (ATCC-No. CCL-86) of said type II anti-CD20 antibody compared to rituximab of 0.3 to 0.6, and in one embodiment, 0.35 to 0.55, and in another embodiment, 0.4 to 0.5.

In one embodiment, said type II anti-CD20 antibody is a GA101 antibody.

In one embodiment, said type II anti-CD20 antibody has increased antibody dependent cellular cytotoxicity (ADCC).

In certain embodiments of the methods of treatment of a cancer in a patient provided herein, the cancer is a non-solid tumor. In one embodiment, the non-solid tumor is a CD20 expressing non-solid tumor. Exemplary non-solid tumors that can be treated in the methods provided herein, include, for instance, a leukemia or a lymphoma. In one embodiment, the non-solid tumor is a B cell lymphoma.

In one embodiment, the CD20 expressing cancer is a B-Cell Non-Hodgkin's lymphoma (NHL).

In one embodiment, said type II anti-CD20 antibody is a monoclonal antibody. The following examples, sequence listing and figures are provided to aid the understanding of the present invention, the true scope of which is set forth in the appended claims. It is understood that modifications can be made in the procedures set forth without departing from the spirit of the invention.

EXAMPLES

Example 1

Treating Lymphoma with a Combination of GDC-0199 and Obinutuzumab.

Nonclinical data supports the hypothesis that the combination of GDC-0199 and GA101 (in this case, obinutuzumab) will show more anti-tumor activity than when each drug is administered alone. The study used a non-Hodgkin's lymphoma (NHL) xenograft model of aggressive lymphoma, the diffuse large B-cell lymphoma (DLBCL) derived cell line SU.DHL-4. Obinutuzumab was administered at a dose of 1 mg/kg IV, once a week for 3 weeks and achieved tumor stasis followed by growth delay. GDC-0199 was administered at 100 mg/kg QD for 21 days and also demonstrated stasis followed by tumor growth delay. However, the combination of GDC-0199 and obinutuzumab induced a greater than additive effect resulting in tumor regressions (5 of 8 partial regressions (PRs); see FIG. 1). Three weeks of combination therapy resulted in enhanced tumor growth inhibition (TGI) (118% TGI), compared with 76% (GA101) and 80%) (GDC 0199) TGI observed with single agent administration (see FIG. 1). Increased tumor regressions (5 PRs) were also observed when GA101 was combined with GDC 0199, compared with single agent administration. Additionally, TGI was sustained in the combination treatment group after treatment ended on day 21 since 116% TGI was observed at day 31 (10 days after dosing ended), versus 30% TGI with GA101 and 25% TGI with GDC 0199 as single agents. In summary, GA101 in combination with GDC 0199 resulted in increased TGI and tumor regressions compared to each agent administered separately in a NHL xenograft model.

In this study the vehicles for GA-101 and GDC-0199 were saline and 60% phosal, respectively. In FIG. 1, the dose of GDC-0199 is expressed as free base equivalents in mg/kg of body weight. Results are expressed as the fitted tumor volume as determined by linear mixed effects modeling for each treatment group vs. time in days, where Day 0 is the first day of treatment.

Example 2

A Phase Ib Multicenter Study of GDC-0199 and Obinutuzumab in Patients with Relapsed or Refractory or Previously Untreated Chronic Lymphocytic Leukemia.

Two schedules will be evaluated: Schedule A (FIG. 2), consisting of GDC-0199 administered in escalating doses for 3 weeks prior to the first obinutuzumab infusion, and Schedule B (FIG. 3), consisting of obinutuzumab administered first followed by escalating dose levels of GDC-0199. Schedule A and Cohort 1 of Schedule B will be enrolled in parallel. In addition, the dose-finding stage will evaluate whether the administration of GDC-0199 prior to the first obinutuzumab infusion (Schedule A) will result in a lower incidence of infusion reactions, thereby reducing the need for split doses of obinutuzumab and corticosteroid premedication.

The expansion stage will include two expansion cohorts of 20 patients each (relapsed/refractory and previously untreated CLL) and will evaluate the safety and preliminary efficacy of the selected combination dose and schedule.

In Schedule A, the combination treatment of GDC-0199 and obinutuzumab will be administered for a total of 7 cycles of 28 days each, including a total of 8 infusions of obinutuzumab and GDC-0199 QD.

In Schedule B, the combination treatment of GDC-0199 and obinutuzumab will be administered for a total of 6 cycles of 28 days each, including a total of 9 infusions of obinutuzumab (8 doses; first dose will be split into two infusions) and GDC-0199 QD. GDC-0199 monotherapy may be continued in patients beyond 6-7 cycles of combination treatment described above (e.g., if they have acceptable toxicity and have not yet achieved maximal clinical response (i.e., are having continued improvement/reduction in tumor burden that has not yet stabilized for at least 2 months)). Such patients may continue GDC-0199 monotherapy until they have achieved maximal response or up to 1 year after the last patient is enrolled, whichever occurs first.

Example 3

Antitumor Activity of Combined Treatment of GDC-0199 and Type II Anti-CD20 Antibody (Obinutuzumab) as Compared to Combined Treatment of GDC-0199 and a Type I Anti-CD20 Antibody (Rituximab).

Test agents. The type II anti-CD20 antibody was the GA101 antibody IgG1 (a chimeric humanized IgG1 antibody as disclosed in WO 2005/044859 (termed B-HH6-B-KV1 GE therein, also known as obinutuzumab or RO5072759), which was provided as stock solution (conc.

9.4 mg/ml) from Roche GlycArt, Schlieren, Switzerland. Antibody buffer included histidine, trehalose and polysorbate 20. Antibody solution was diluted appropriately in PBS from stock for prior injections. GDC-0199 was obtained from Genentech Inc., Calif., USA.

Cell line and culture conditions. The human Z138 mantle cell lymphoma cell line is routinely cultured in DMEM supplemented with 10% fetal bovine serum (PAA Laboratories, Austria) and 2 mM L-glutamine at 37° C. in a water-saturated atmosphere at 5% $C_2$. Cells were co-injected with MATRIGEL.

Animals. Female SCID beige mice; age 5-6 weeks at arrival (purchased from Charles River, Sulzfeld, Germany) were maintained under specific-pathogen-free condition with daily cycles of 12 h light/12 h darkness according to committed guidelines (GV-Solas; Felasa; TierschG). Experimental study protocol was reviewed and approved by local government (Regierung von Oberbayern; registration no. 55.2-1-54-2531.2-26-09). After arrival animals were maintained in the quarantine part of the animal facility for one week to get accustomed to new environment and for observation. Continuous health monitoring was carried out on regular basis. Diet food (Altromin Spezialfutter GmbH & Co. KG) and water (filtered) were provided ad libitum.

Monitoring. Animals were controlled daily for clinical symptoms and detection of adverse effects. For monitoring throughout the experiment body weight of animals was documented two times weekly and tumor volume was measured by caliper after staging.

Treatment of animals. Animal treatment was started at the day of randomisation 18 days after tumor cell inoculation. RO5072759 or rituximab were administered as single agent, i.p., once weekly (day 18, 25, 32) for 3 weeks at dosages of 1 mg/kg. The corresponding vehicle was administered on the same days. GCD-0199 was given p.o. once daily (from day 18 to day 34), over 17 days at a dosage of 100 mg/kg. In the combination therapy groups, the antibodies and GDC-0199 were administered at the same dosages and on the same days.

Tumor growth inhibition study in vivo. Results of therapy on tumor volume development are shown in FIG. 4. On day 35 after tumor cell inoculation, there was a tumor growth inhibition of 32%, 59%, 73%, 96% or 106%) (regression) in the animals given rituximab, GDC-0199, RO5072759, combination of GDC-0199 plus rituximab or combination of GDC-0199 plus RO5072759, respectively, compared to the control group.

Example 4

Administration of GDC-0199 as a Single Agent Following Combination with Obinutuzumab Results in Significant Delay in Tumor Regrowth.

This example describes results using the DLBCL SU-DHL-4 xenograft model, which discussed in Example 1 above. Initially, GDC-0199 was dosed orally for 21 continuous days in combination with GA101 (in this example, obinutuzumab) at 1 mg/kg for 3 weeks. The latter resulted in enhanced TGI (91%), compared with 54% (GA101) and 24% (GDC-0199) TGI observed with each agent alone (FIG. 5). At day 22 tumor bearing mice in the combination cohort continued to be dosed with GDC-0199 alone at 100 mg/kg for an additional 24 days. The latter resulted in a significant delay in tumor regrowth when compared to mice treated with the combination of GA101 and GDC-0199 over a 21 day period (time to tumor progression of the combination cohort=38 days vs. continued treatment with GDC-0199=45 days (FIG. 5). Thus, single-agent treatment with GDC-0199 following combination with GA101 sustains efficacy in vivo. These results support a benefit for maintenance therapy with GDC-0199.

In FIG. 5, the control is saline vehicle for GA101 plus 60% phosal vehicle for GDC-0199. GA101 was dosed intravenously once a week (QW) for 3 weeks and GDC-0199 was dosed orally and daily (QD) for 21 days (QD×21) as single agents or in combination. As explained above, a cohort of tumor bearing mice was also dosed with GDC-0199 alone for an additional 24 days after combination treatment ended on day 21 (QD×45). Under the x-axis, treatment periods are denoted by solid black lines (—) for the combination cohorts while the continued single agent GDC-0199 treatment is denoted by dashed black line (———).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for the treatment of chronic lymphocytic leukemia in a human patient suffering from relapsed or refractory or previously untreated chronic lymphocytic leukemia, said method comprising
co-administering to the patient an effective amount of a compound, which is 2-(1H-pyrrolo[2,3-b]pyridin-5-yloxy)-4-(4-((2-(4-chlorophenyl)-4,4-dimethylcyclohex-1-enyl)methyl)piperazin-1-yl)-N-(3-nitro-4-(((tetrahydro-2H-pyran-4-yl)methyl)amino)phenylsulfonyl)benzamide, and obinutuzumab, in multiple dosing cycles, wherein
i) each dosing cycle of the multiple dosing cycles is 28 days;
ii) the obinutuzumab is administered once a week for two or more weeks of the first dosing cycle and is administered once per dosing cycle after the first dosing cycle of the multiple dosing cycles;
iii) the compound is administered to the human in daily doses beginning in the first dosing cycle; and
iv) the amount of the compound in the daily doses increases from a first amount administered in the first dosing cycle to a second amount administered to the human in dosing cycles after the first dosing cycle; followed by
administering to the patient daily doses of the compound alone in the absence of the obinutuzumab.

2. The method of claim 1, wherein the first dose of the obinutuzumab administered to the human is administered as a split dose on day 1 and day 2 of the first dosing cycle.

3. The method of claim 2, wherein the compound is administered to the human in daily doses beginning in the first dosing cycle after the first administration of the obinutuzumab.

4. The method of claim 3, wherein the first amount of the compound administered to the human is between 10 mg to 80 mg per dose and the second amount is between 190 mg to 400 mg per dose.

5. The method of claim 4, wherein the effective amount of the obinutuzumab is from 500 mg to 3000 mg.

6. The method of claim 5, wherein both the obinutuzumab and the compound are co-administered to the human for 6 cycles of the multiple dosing cycles.

7. The method of claim 4, wherein the second amount of the compound administered to the human is 400 mg.

8. The method of claim 7, wherein the effective amount of the obinutuzumab is 1000 mg.

9. The method of claim 8, wherein both the obinutuzumab and the compound are co-administered to the human for 6 cycles of the multiple dosing cycles.

10. The method of claim 1, wherein the chronic lymphocytic leukemia is a CD20-expressing chronic lymphocytic leukemia.

* * * * *